US00PP11033P

United States Patent [19]

Lyrene

[11] Patent Number: Plant 11,033

[45] Date of Patent: Aug. 17, 1999

[54] BLUEBERRY PLANT CALLED 'BLUECRISP'

[76] Inventor: Paul M. Lyrene, University of Florida, P.O. Box 110690, Gainesville, Fla. 32611-0690

[21] Appl. No.: 08/956,629

[22] Filed: Aug. 18, 1997

[51] Int. Cl.[6] ..... A01H 5/00

[52] U.S. Cl. ..... Plt./157

[58] Field of Search ..... Plt./157

[56] References Cited

U.S. PATENT DOCUMENTS

| | | | |
|---|---|---|---|
| P.P. 7,974 | 9/1992 | Lyrene | Plt./157 |
| P.P. 9,834 | 3/1997 | Lyrene | Plt./157 |
| P.P. 10,675 | 11/1998 | Lyrene | Plt./157 |
| P.P. 10,788 | 2/1999 | Lyrene | Plt./157 |

*Primary Examiner*—Howard J. Locker
*Assistant Examiner*—Kent L. Bell

[57] ABSTRACT

A new and distinct low-chill, tetraploid highbush blueberry (Vaccinium) variety of complex ancestry, based largely on *V. corymbosum* L. with some genes from *V. darrowi* Camp. Its novelty consists of the following unique combination of features:

1. Produces fruit which, when chilled to 10° C., has a distinct crisp or crunchy texture.
2. Flowers and leafs vigorously in Florida in areas where the mean temperature of the coldest month is 58° F. or colder.
3. Ripens its fruit 60 days after flowering in north-central Florida.
4. Ripens 80% of its fruit between April 20 and May 15 in north-central Florida.
5. Produces fruit that are large, firm, have a good picking scar, and a good flavor.
6. Produces a bush that is semi-upright and vigorous, with good resistance to *Phytophthora cinnamomi* and *Botryosphaeria dothedia*.
7. Can readily be propagated by softwood cuttings.

2 Drawing Sheets

ORIGIN OF THE VARIETY

'Bluecrisp' originated as a seedling in the University of Florida blueberry breeding program in Gainesville, Fla. 'Bluecrisp' and both its pollen and its seed parent are mainly *Vaccinium corymbosum* L., but 'Bluecrisp' and both of its parents have some genes from *Vaccinium darrowi* Camp. The cross from which the original plant was grown was made in a greenhouse in Gainesville in March 1980. Because the seeds from a large number of crosses were bulked before planting, the exact seed and pollen parents that gave rise to 'Bluecrisp' are not known. However, both parental clones were products of a long-term recurrent selection program in which characteristics of northern highbush varieties were being combined with characteristics of *V. darrowi,* a native Florida species. None of the clones used in any of the crosses that produced the bulk was patented. The original plant of 'Bluecrisp' was selected in 1984, after it fruited in a field nursery in Gainesville, Fla., where it was being evaluated along with approximately 10,000 seedlings of other genotypes. A 15-plant test plot of asexually propagated plants was established in Gainesville in 1986. Other plants from rooted cuttings were planted at test locations in Interlachen, Fla., and at Homerville, Ga. The clone was selected as a useful cultivar based on superior berry and plant qualities manifested at these sites between 1986 and 1997.

ASEXUAL PROPAGATION OF THE VARIETY

The new and distinct variety has been propagated by softwood cuttings on numerous occasions. In every case, all the resulting plants have displayed the varietal characteristics without exception.

SUMMARY OF THE VARIETY

'Bluecrisp' is vigorous and produces a semi-upright plant with a low chill requirement. Although its chromosome number has not been determined cytologically, both the genetic stocks from which it was developed, its pedigree, and its crossing behavior indicate that it is tetraploid (2N=4×=48). 'Bluecrisp' has been crossed on numerous occasions with other tetraploid cultivars, and the number of viable seedlings produced per pollinated flower has been high, whether it was used as the pollen or the seed parent. 'Bluecrisp' breaks both leaf and flower bud without delay in the spring, even after abnormally mild winters in Gainesville, Fla., where the mean January temperature is 56° F. with an average of about 400 hours per winter of temperatures below 45° F. Because of its low chilling requirement and early flowering time, crop losses due to March and early-April freezes could be excessive when 'Bluecrisp' is grown in the southeastern United States north of a line from Savannah, Ga., to Shreveport, La. The plant has moderate to high tolerance to the two most serious diseases of highbush blueberries in the southeastern United States, Phytophthora root rot and Botryosphaeria stem blight. The flower buds are susceptible to the blueberry bud mite (*Acalitus vaccinii* Keifer), and chemical control may be necessary to obtain high yields where this mite is present. The mean date of 50% anthesis at Gainesville for the 4 seasons 1994 through 1997 was February 26 (range February 22 to March 3). The mean date of 50% ripe fruit at Gainesville for the same years was April 28 (range April 15 to May 4). Berries are large (2.2 g per berry) and dark blue in color. The small, dry pedicel scar and the unusually high firmness combine to give the berries a long post-harvest life. Both flavor and texture were rated high in organoleptic tests. 'Bluecrisp' has the following unique combination of features:

1. Produces fruit which, when chilled to 10° C., has a distinct crisp or crunchy texture.

2. Flowers and leafs vigorously in Florida in areas where the mean temperature of the coldest month is 58° F. or colder.

3. Ripens its fruit 60 days after flowering in north-central Florida.

4. Ripens 80% of its fruit between April 20 and May 15 in north-central Florida.

5. Produces fruit that are large, firm, have a good picking scar, and a good flavor.

6. Produces a bush that is semi-upright and vigorous, with good resistance to *Phytophthora cinnamomi* and *Botryosphaeria dothidia.*

7. Can be propagated readily by softwood cuttings.

DESCRIPTION OF THE VARIETY

Figure 1:
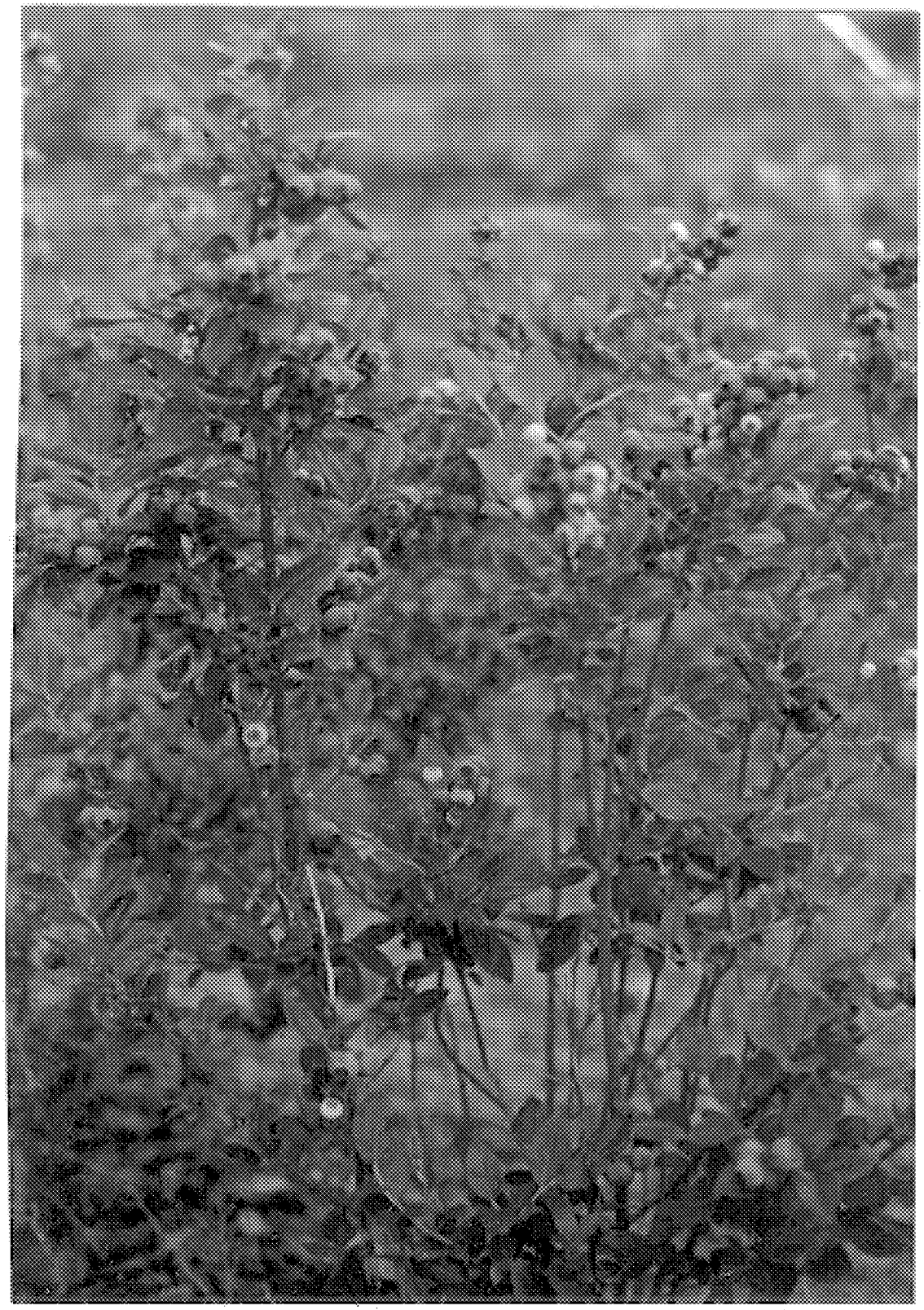
FIG. 1 illustrates a 4 year old specimen of the plant 'Bluecrisp' in side elevation and shows the multiple trunk and branch scaffolding and also depicts the canopy and fruit clusters of the plant at a seasonal stage during the harvest period in late April in north central Florida.
Figure 2:
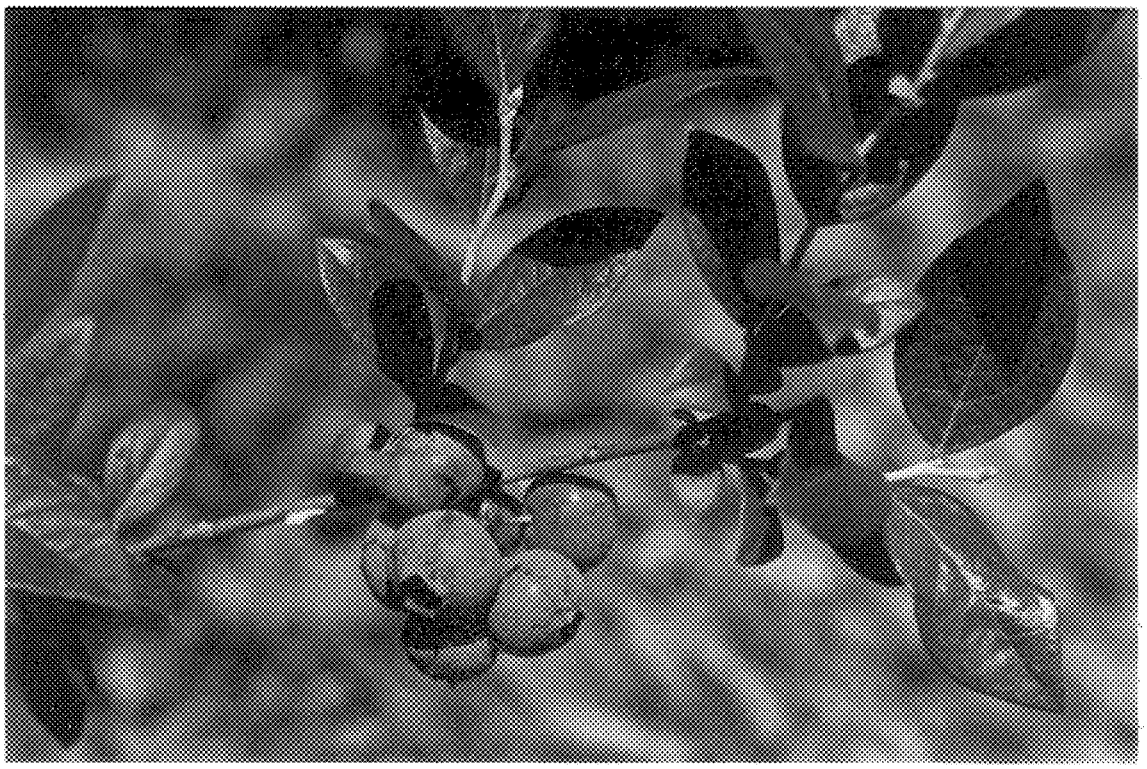
FIG. 2 shows in larger scale a fruit cluster of 'Bluecrisp' as well as the top surface of foliage along with the character and color of wood of fruiting age.
Figure 3:
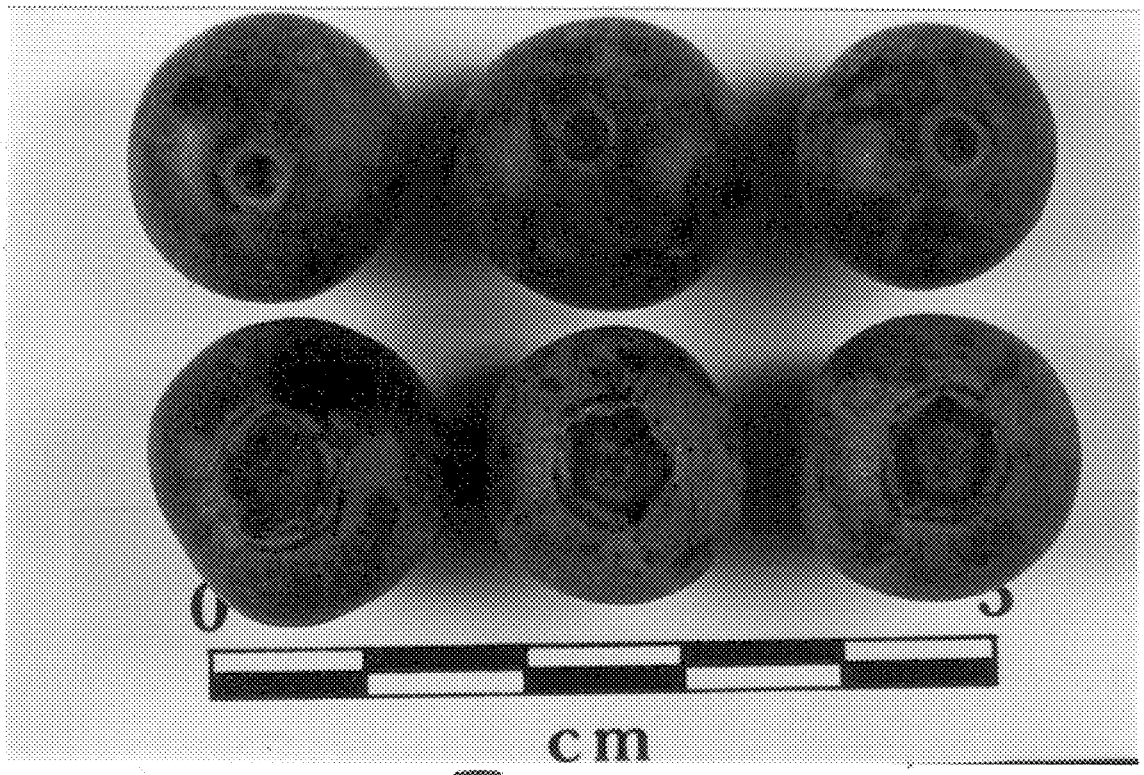
FIG. 3 shows an even closer scale of the berries of 'Bluecrisp' including the pedicel scar and the calyx tube aperture of the mature fruit.

The following is a detailed botanical description of the new and distinct variety of blueberry, its flowers, fruit and foliage, based on observation of specimens grown in Gainesville, Fla. Color descriptions, except those given in common terms, use terminology from "The Pantone Book of Color", 1990, by Leatrice Eiseman and Lawrence Herbert; Harry N. Abrams, Inc. Publishers, New York.

Bush:

*Size.*—Large; on good soil, plants reach 1 m tall with a canopy diameter of 1 m within 3 years. Eventual height is over 2 m.

*Vigor.*—Medium to high.

*Growth habit.*—Between upright and spreading.

*Productivity.*—Medium to high; yields about 4 pounds of berries per plant on 4-year-old plants.

*Flower buds.*—Moderately numerous.

Trunk:

*Suckering tendency.*—Medium to copious sprouting from the base. Four-year plants have 4 to 10 major trunks from the ground if not pruned.

*Texture.*—Bark on older trunks rough, but exfoliates to smooth.

*Color.*—"Cement" (Pantone 14-0708).

Twigs:

*Color.*—Current-season twigs in full sun "white jade" in June (Pantone 12-0315). Two-year old twigs in full sun "peach" in June (Pantone 14-1227).

*Internode length.*—For new shoots of moderate vigor averages 15 mm.

Leaves:

*Size.*—Length of typical leaves 60 mm; Width of typical leaves 34 mm.

*Shape.*—Ovate, apically acute.

*Margin.*—Entire.

*Color of upper surface.*—"Chive" (Pantone 19-0323).

*Color of lower surface.*—"Sage green" (Pantone 15-0318).

*Pubescence, upper surface.*—Numerous short, white hairs on midrib and major veins.

*Pubescence, lower surface.*—Inconspicuous or absent.

*Pubescence, leaf margins.*—Inconspicuous or absent.

Flowers:

*Corolla.*—Consists of 5 petals fused into a corolla tube as is typical for *V. corymbosum.*

*Length, bottom of ovary to corolla tip.*—13.5 mm.

*Diameter of corolla at widest point.*—9.0 mm.

*Corolla aperture diameter.*—4.0 mm.

*Gynoecium and androecium.*—Typical of *V. corymbosum.*

*Color at anthesis.*—"Chalk" (Pantone 12-2902).

*Fragrance.*—None.

*Pollen production.*—Copious.

*Flowering period.*—Early (Mid Feb. to Mid March, N. Florida).

*Inflorescence morphology.*—Pedicel length 5–10mm; peduncle length 10–20mm, giving a moderately loose fruit cluster.

*Self compatibility.*—Partially self compatible but must be cross- pollinated with another tetraploid cultivar for full productivity.

Berry:

*Size.*—Large, about 2.2 g per berry.

*Height.*—14.1 mm.

*Width.*—16.2 mm.

*Diameter calyx aperture, mature berry.*—8.1 mm.

*Color.*—Dapple grey (Pantone 16-3907).

*Color of skin without waxy bloom.*—Dark navy (Pantone 19-4013).

*Pedicel scar.*—Small and dry.

*Firmness.*—Extremely firm, with a crunchy texture.

*Flavor.*—Sweet with slight acidity.

*Texture.*—Good: small seeds, thin skin, few sclerids.

*Wax.*—Moderately persistent.

*Maturity date.*—Early-season. Mid-harvest averages May 2 in Gainesville, Fla.

*Clusters.*—Normally 5 to 8 berries per cluster.

I claim:

1. A new and distinct highbush blueberry plant, substantially as illustrated and described, characterized by its low chilling requirement, large fruit, high fruit quality, extremely firm (crunchy) berry texture, early ripening, and resistance to Phytophthora root rot and Botryosphaeria stem blight, having the ability to be asexually propagated by softwood cuttings.

* * * * *